United States Patent
Meguro (10) Patent No.: US 12,260,554 B2
(45) Date of Patent: Mar. 25, 2025

(54) ENDOSCOPIC IMAGE PROCESSING APPARATUS

(71) Applicant: FUJIFILM Corporation, Tokyo (JP)

(72) Inventor: Misaki Meguro, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 384 days.

(21) Appl. No.: 18/058,830

(22) Filed: Nov. 25, 2022

(65) Prior Publication Data

US 2023/0091729 A1   Mar. 23, 2023

Related U.S. Application Data (63) Continuation of application No. PCT/JP2021/020228, filed on May 27, 2021.

(30) Foreign Application Priority Data

May 27, 2020 (JP) .................. 2020-092566

(51) Int. Cl.
G06T 7/00 (2017.01)
A61B 1/00 (2006.01)

(52) U.S. Cl.
CPC ...... G06T 7/0012 (2013.01); A61B 1/000096 (2022.02); G06T 2207/10068 (2013.01); G06T 2207/30092 (2013.01)

(58) Field of Classification Search
CPC ......... G06T 7/0012; G06T 2207/10068; G06T 2207/30092; A61B 1/000096
USPC ........................................ 382/128
See application file for complete search history.

(56) References Cited

U.S. PATENT DOCUMENTS

| 5,187,579 A | 2/1993 | Hiyama |
|---|---|---|
| 2018/0220873 A1 | 8/2018 | Tani |
| 2018/0242817 A1 | 8/2018 | Imaizumi et al. |
| 2019/0175000 A1 | 6/2019 | Peleg |
| 2019/0387962 A1 | 12/2019 | Nakamitsu et al. |
| 2020/0065614 A1 | 2/2020 | Nishimura |
| 2020/0138269 A1* | 5/2020 | Nishimura ........... A61B 1/0005 |

(Continued)

FOREIGN PATENT DOCUMENTS

| JP | H03-293393 A | 12/1991 |
|---|---|---|
| JP | 2012-152333 A | 8/2012 |

(Continued)

OTHER PUBLICATIONS

International Search Report issued in PCT/JP2021/020228; mailed Aug. 10, 2021.

(Continued)

*Primary Examiner* — Gabriel I Garcia
(74) *Attorney, Agent, or Firm* — Studebaker Brackett PLLC (57) ABSTRACT

In a case where a first specific scene recognized at a time of insertion of an endoscope is stored in a specific scene memory and a recognized scene recognized by a scene recognition unit is a scene on a side deeper than the first specific scene in a direction of movement of the endoscope, the recognized scene is output without being changed. In a case where the first specific scene is stored in the specific scene memory and the recognized scene is a scene on a side shallower than the first specific scene in the direction of movement of the endoscope, the recognized scene is changed and output.

15 Claims, 10 Drawing Sheets

(56) References Cited

U.S. PATENT DOCUMENTS

| | | | | |
|---|---|---|---|---|
| 2021/0212790 A1* | 7/2021 | Yoshimura | ............. | A61B 5/065 |
| 2022/0230303 A1* | 7/2022 | Karaoglu | ................ | A61B 34/20 |
| 2022/0334454 A1* | 10/2022 | Veit | ........................ | A61B 1/041 |

FOREIGN PATENT DOCUMENTS

| | | |
|---|---|---|
| JP | 2017-108792 A | 6/2017 |
| JP | 2019-097661 A | 6/2019 |
| WO | 2017/061495 A1 | 4/2017 |
| WO | 2017/073338 A1 | 5/2017 |
| WO | 2018/135041 A1 | 7/2018 |
| WO | 2019/064704 A1 | 4/2019 |

OTHER PUBLICATIONS

International Preliminary Report on Patentability (Chapter I) and Written Opinion of the International Searching Authority issued in PCT/JP2021/020228; issued Nov. 17, 2022.

\* cited by examiner

(SCENE RECOGNITION UNIT)

(SCENE OUTPUT UNIT)

(ORDER OF EXAMINATION IN FORWARD PATH)

FIG. 17

ENDOSCOPIC IMAGE PROCESSING APPARATUS

CROSS-REFERENCE TO RELATED APPLICATIONS

This application is a Continuation of PCT International Application No. PCT/JP2021/020228 filed on 27 May 2021, which claims priority under 35 U.S.C § 119(a) to Japanese Patent Application No. 2020-092566 filed on 27 May 2020. The above application is hereby expressly incorporated by reference, in its entirety, into the present application.

BACKGROUND OF THE INVENTION

1. Field of the Invention

The present invention relates to an endoscopic image processing apparatus that performs recognition processing using artificial intelligence (AI).

2. Description of the Related Art

In the medical field, medical image processing systems that perform processing on medical images, such as an endoscope system having an endoscope, a light source device, and a processor device, are widely used. In recent years, the AI technology has started to be used to detect a lesion area from a medical image (for example, WO2017/073338A (corresponding to US2018/242817A1)) or to recognize a lesion and classify the type of the lesion for the purpose of preventing oversight of a lesion or reducing a burden on a user.

SUMMARY OF THE INVENTION

In a medical image processing system that performs recognition processing of lesions, parameters or internal processing corresponding to a site or an organ that is an actually observed scene may be selected to correctly perform the recognition processing. For this purpose, the recognition processing of a scene may be performed on the basis of features of an image. Even in the recognition processing of scenes, however, depending on the scene to be observed, a scene different from the actual scene may be recognized. For example, digestive tracts such as an esophagus, a stomach, and a large intestine may be incorrectly recognized.

JP2012-152333A discloses a technique for observation with an endoscope, in which sites such as the esophagus, gastric cardia, and stomach are determined from captured image data and the illumination mode is automatically switched to an illumination mode corresponding to each of the sites to perform illumination suitable for the respective site.

In the techniques of the related art, as in WO2017/073338A, it is necessary to identify a scene in an observation image to detect a lesion area from the observation image. However, in a case where a large number of observation images are acquired as in a screening examination, a problem occurs in that determination of whether each observation image shows an appropriate scene imposes a heavy burden on a user. As in JP2012-152333A, in a case where a scene is automatically recognized and the next processing is performed in response to the recognition of the scene, a problem occurs in that an incorrect recognition of a scene may result in the execution of processing unintended by the user.

It is an object of the present invention to provide an endoscopic image processing apparatus capable of accurately recognizing a scene to be used in lesion recognition processing.

To address the problems described above, an endoscopic image processing apparatus according to the present invention is an endoscopic image processing apparatus including a processor. The processor is configured to acquire an endoscopic observation image captured by an endoscope having an insertion portion to be inserted into a body cavity of a subject, the endoscopic observation image being an observation image of an inside of the body cavity; recognize a scene by using the endoscopic observation image; in a case where a recognized scene recognized by the processor is a first specific scene recognized at a time of insertion of the insertion portion, store the recognized scene in a specific scene memory as the first specific scene; output the recognized scene without changing the recognized scene in a case where the first specific scene is stored in the specific scene memory and the recognized scene is a scene on a side deeper than the first specific scene in a direction of movement of the insertion portion; and change the recognized scene and output the changed recognized scene in a case where the first specific scene is stored in the specific scene memory and the recognized scene is a scene on a side shallower than the first specific scene in the direction of movement of the insertion portion.

When changing the recognized scene, preferably, the processor is configured to change the recognized scene to a scene on the side deeper than the first specific scene.

Preferably, the processor is configured to change the recognized scene to a scene on the side deeper than the first specific scene in a case where the first specific scene is stored in the specific scene memory and the recognized scene is not a scene associated with the first specific scene.

Preferably, the processor is configured to change the recognized scene to a scene associated with the first specific scene in a case where the first specific scene is stored in the specific scene memory and the recognized scene is not a scene associated with the first specific scene.

Preferably, the processor is configured to change the recognized scene to a scene having a high degree of certainty among scenes on the side deeper than the first specific scene.

In a case where the recognized scene is a second specific scene at a position where the insertion portion is pulled back in the direction of movement of the insertion portion, preferably, the processor is configured to store the recognized scene in the specific scene memory as the second specific scene.

Preferably, the processor is configured to output the recognized scene without changing the recognized scene in a case where the second specific scene is stored in the specific scene memory.

In a case where the recognized scene is a third specific scene recognized at a time of removal of the insertion portion, preferably, the processor is configured to store the recognized scene in the specific scene memory as the third specific scene.

Preferably, the processor is configured to change the recognized scene and output the changed recognized scene in a case where the recognized scene is a scene on the side deeper than the third specific scene.

When changing the recognized scene, preferably, the processor is configured to change the recognized scene by using a recognized scene changed by the processor.

Preferably, the scene includes at least one of a pharynx, an esophagus, an esophagogastric junction, a stomach, or a duodenum.

Preferably, the first specific scene is any one of an esophagus, an esophagogastric junction, or a stomach at the time of insertion of the insertion portion.

Preferably, the second specific scene is a duodenum.

Preferably, the third specific scene is any one of an esophagus, an esophagogastric junction, or a stomach at the time of removal of the insertion portion.

Preferably, the processor is configured to perform lesion recognition processing, the lesion recognition processing being recognition processing for detecting a lesion included in the endoscopic observation image by using the recognized scene that is output.

According to the present invention, it is possible to accurately recognize a scene used in lesion recognition processing.

DESCRIPTION OF THE PREFERRED EMBODIMENTS

Figure 1:
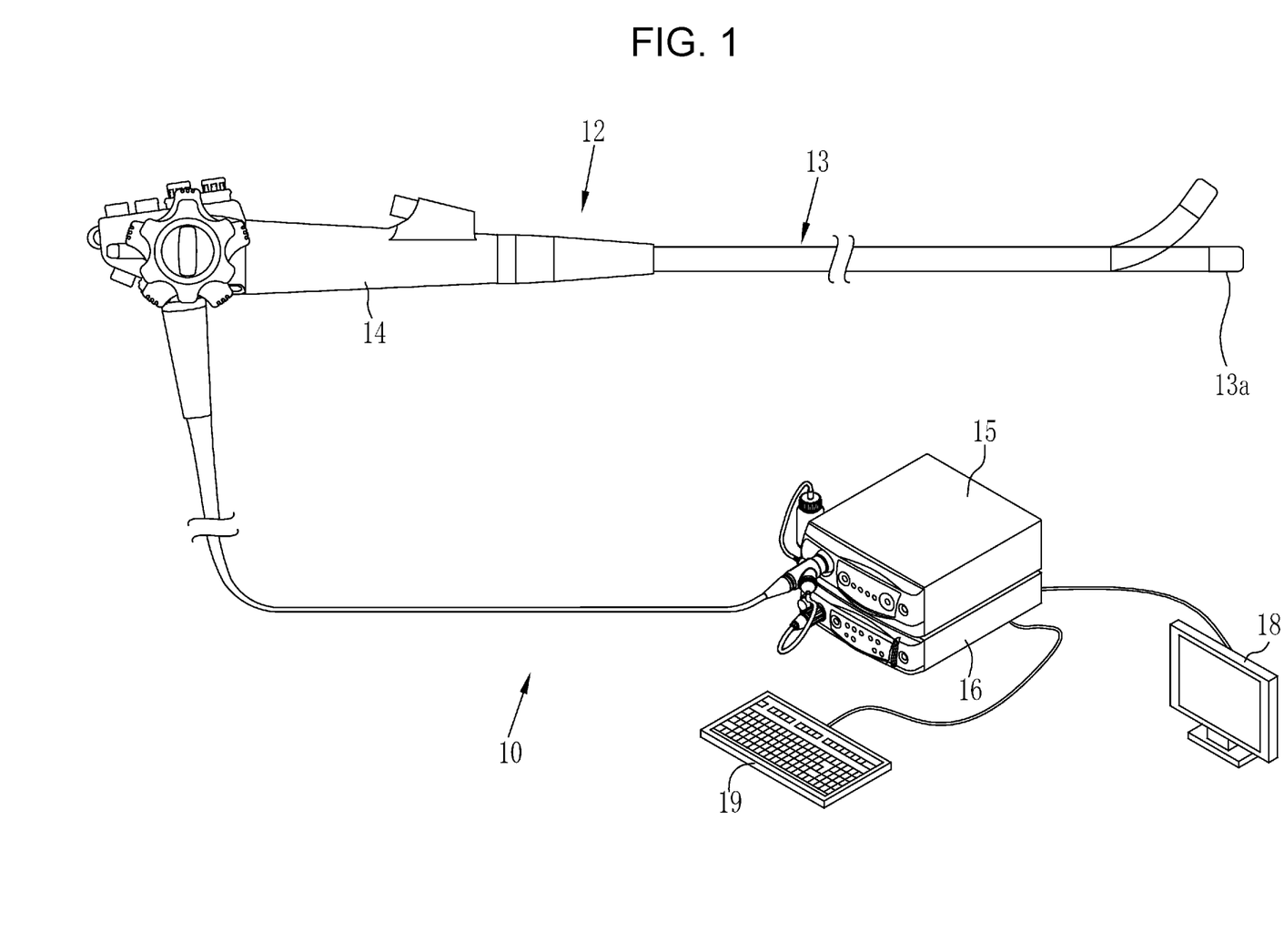
FIG. 1 is an external view of an endoscope system.

As illustrated in FIG. 1, an endoscope system 10 has an endoscope 12, a light source device 15, an endoscopic image processing apparatus 16, a monitor 18, and a console 19. The endoscope 12 has an insertion portion 13 to be inserted into a body cavity of a subject and an operation portion 14 for operating the endoscope 12. In response to an operation of the operation portion 14, a tip part 13a of the insertion portion 13 is directed in a desired direction, and an image capturing unit (not illustrated) having a built-in imaging device, such as a charge-coupled device (CCD), of the tip part 13a is used to capture an image of the inside of the body cavity of the subject to acquire an observation image. The light source device 15 controls illumination light such as normal light and special light used for illumination of an observation target. The endoscopic image processing apparatus 16 is electrically connected to the monitor 18 and the console 19. The monitor 18 displays an observation image output from the endoscopic image processing apparatus 16, information attached to the observation image, and so on. The console 19 receives input operations such as designation of a region of interest and setting of functions.

Figure 2:
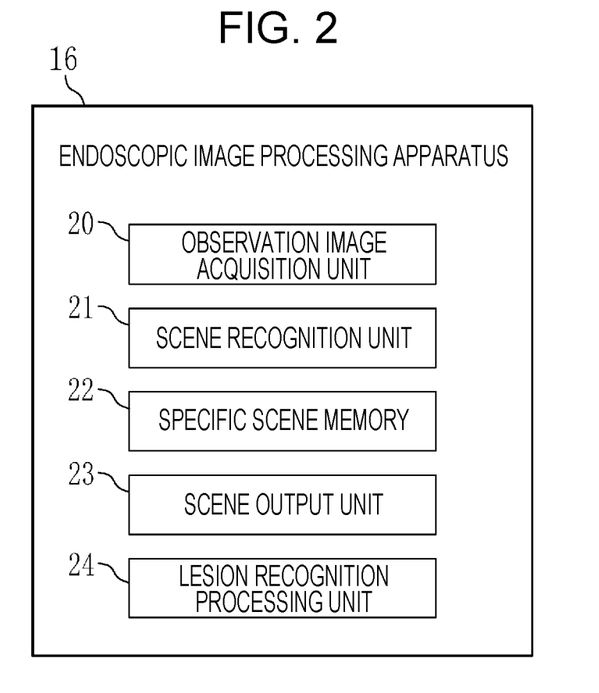
FIG. 2 is a block diagram illustrating functions of an endoscopic image processing apparatus.

As illustrated in FIG. 2, the endoscopic image processing apparatus 16 has an observation image acquisition unit 20, a scene recognition unit 21, a specific scene memory 22, a scene output unit 23, and a lesion recognition processing unit 24. In the endoscopic image processing apparatus 16, a program related to lesion recognition processing is incorporated in a program memory. The program is operated by a control unit (not illustrated), which is constituted by a processor, to implement the functions of the observation image acquisition unit 20, the scene recognition unit 21, the specific scene memory 22, the scene output unit 23, and the lesion recognition processing unit 24.

The observation image acquisition unit 20 captures an image of an observation target to acquire an observation image. The scene recognition unit 21 recognizes a scene in the observation image. When a recognized scene recognized by the scene recognition unit 21 is a first specific scene in a forward path F, the specific scene memory 22 stores the recognized scene as a first specific scene. In a case where the first specific scene is stored in the specific scene memory 22 and the recognized scene is a scene on the side deeper than the first specific scene in the direction of movement of the insertion portion 13, the scene output unit 23 outputs the recognized scene without changing the recognized scene. In a case where the first specific scene is stored in the specific scene memory 22 and the recognized scene is a scene on the side shallower than the first specific scene in the direction of movement of the insertion portion 13, the scene output unit 23 changes the recognized scene and outputs the changed recognized scene. The recognized scene output from the scene output unit 23 is input to the lesion recognition processing unit 24, and the lesion recognition processing unit 24 performs lesion recognition processing corresponding to each scene by using the input recognized scene. The forward path F refers to a direction in which the insertion portion 13 is inserted in the direction of movement of the insertion portion 13.

Figure 3:
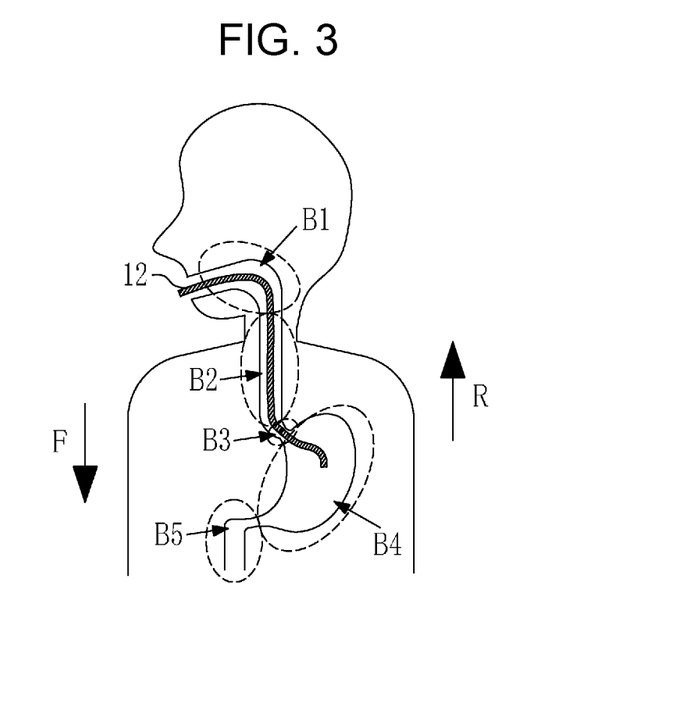
FIG. 3 is an explanatory diagram illustrating the upper digestive tract.

As illustrated in FIG. 3, in the screening of the upper digestive tract using the endoscope 12, the tip part 13a of the endoscope 12 is inserted into the subject through the subject's mouth, and the examination of the forward path F is performed in the order of a pharynx B1, an esophagus B2, an esophagogastric junction (EGJ) B3, a stomach B4, and a duodenum B5. When the tip part 13a of the endoscope 12 reaches the duodenum B5, the tip part 13a of the endoscope 12 is pulled back to perform the examination of a return path R in the order of the duodenum B5, the stomach B4, the esophagogastric junction B3, the esophagus B2, and the pharynx B1. The return path R is a direction opposite to the direction in which the insertion portion 13 is inserted, and refers to a direction in which the insertion portion 13 is removed.

Figure 4:
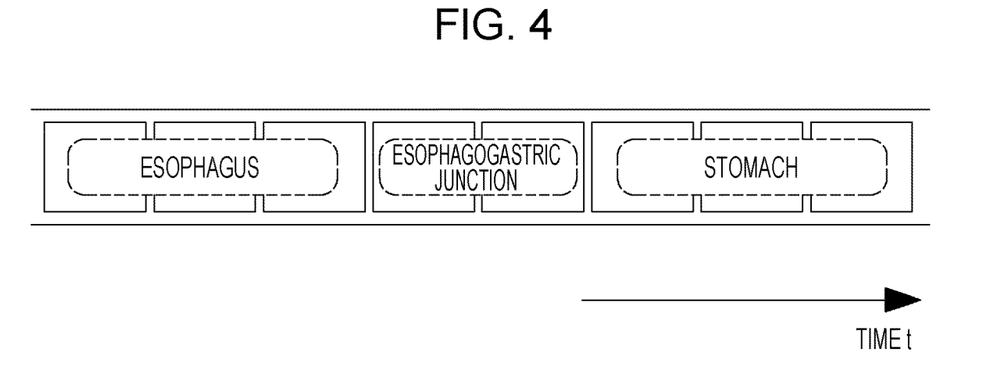
FIG. 4 is an explanatory diagram illustrating observation images of an esophagus, an esophagogastric junction, and a stomach in chronological order.

A user pushes the tip part 13a of the endoscope 12 into the upper digestive tract to capture observation images of sites in the upper digestive tract while causing the tip part 13a of the endoscope 12 to pass through the sites in the upper digestive tract. The observation image acquisition unit 20 acquires the captured observation images. FIG. 4 illustrates an observation image obtained at a certain time t. Observation images acquired by the observation image acquisition unit 20 at times t1, t2, and t3 (see FIG. 5) show captured images of the esophagus B2, the esophagogastric junction B3, and the stomach B4, respectively. A larger number indicating the time t indicates a later time.

The scene recognition unit 21 recognizes a scene in an observation image obtained at each time to acquire a recognized scene. The scene recognition unit 21 acquires the recognized scene on the basis of a difference in the appearance of a mucous membrane, such as a color tone or a shape. However, the scene recognition unit 21 may fail to recognize an appropriate scene in a case such as when a lesion is present in an observation image and a color tone is different from a normal color tone. If an appropriate recognized scene is not obtainable, the scene output unit 23 changes the recognized scene. If the recognized scene is appropriate, the scene output unit 23 outputs the recognized scene without changing the recognized scene.

The lesion recognition processing unit 24 performs lesion recognition processing, which is set for the scene output from the scene output unit 23, on the observation image acquired by the observation image acquisition unit 20. The lesion recognition processing involves detecting the presence or absence of a lesion, the degree of malignancy, and the like in the observation image. The lesion recognition processing may be processing using a training model based on machine learning or the like. Preferred examples of the machine learning method include a convolutional neural network (CNN). In this embodiment, an accurate recognized scene that is suitable for an actual scene is input from the scene output unit 23 to the lesion recognition processing unit 24, thus enabling the lesion recognition processing unit 24 to perform appropriate lesion recognition processing suitable for the actual scene. In the screening using the endoscope 12, it is preferable that lesion recognition processing is performed in parallel with acquisition of observation images.

The scene recognition unit 21 and the scene output unit 23 will be described in detail below. When the scene recognition unit 21 recognizes a scene in the observation image as a specific scene, the specific scene memory 22 stores which specific scene has been recognized. The specific scene memory 22 stores the esophagogastric junction B3 on the forward path F as a first specific scene, the duodenum B5 as a second specific scene, and the esophagogastric junction B3 on the return path R as a third specific scene.

Figure 5:
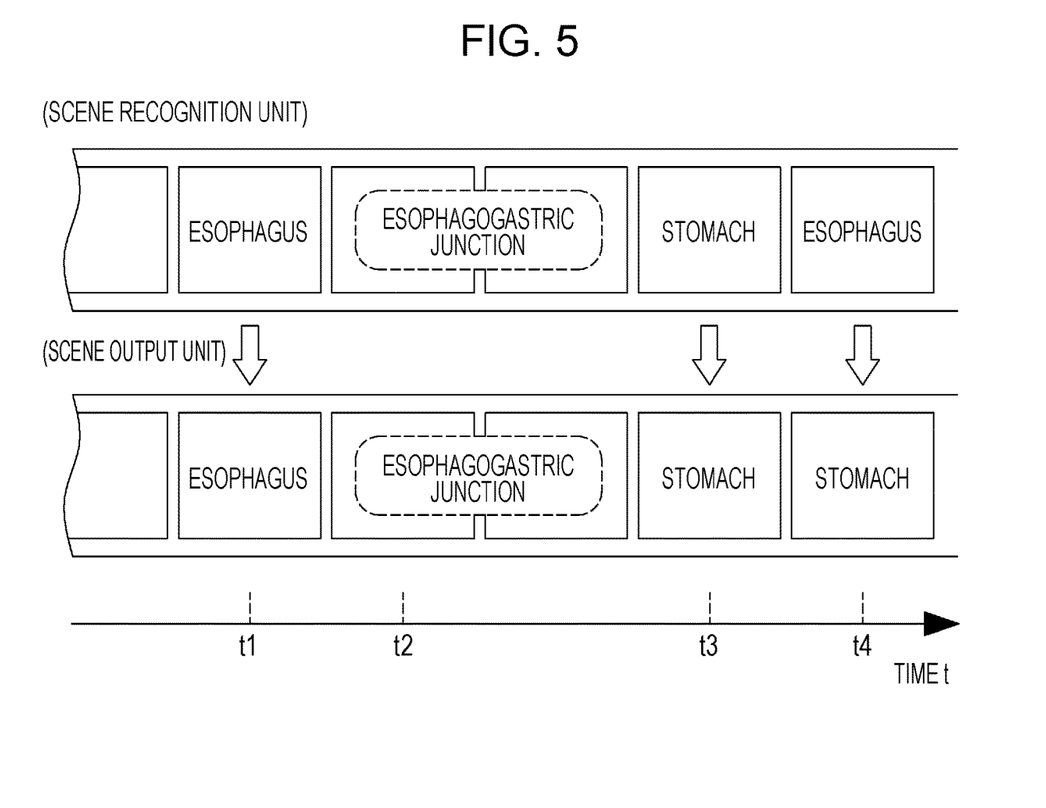
FIG. 5 is an explanatory diagram illustrating functions of a scene recognition unit and a scene output unit in a forward path.

After the insertion of the endoscope 12, the tip part 13a of the endoscope 12 has not reached the esophagogastric junction B3 at time t1 in FIG. 5. In the period during which the tip part 13a of the endoscope 12 does not reach the esophagogastric junction B3, the scene recognition unit 21 does not recognize the esophagogastric junction B3. Thus, no specific scene is stored in the specific scene memory 22. At time t2 in FIG. 5, when the tip part 13a of the endoscope 12 reaches the esophagogastric junction B3 and the scene recognition unit 21 recognizes the esophagogastric junction B3, the specific scene memory 22 stores the esophagogastric junction B3 as a first specific scene.

After the tip part 13a of the endoscope 12 has passed through the esophagogastric junction B3, as at time t3 in FIG. 5, the scene recognition unit 21 recognizes that the scene is the stomach B4. If the image includes a lesion or the like, the scene recognition unit 21 may fail to recognize an appropriate scene. For example, at time t4 in FIG. 5, although an image of the stomach B4 is actually captured, the scene recognition unit 21 erroneously recognizes it as the esophagus B2.

Accordingly, after the first specific scene is stored in the specific scene memory 22, the scene output unit 23 does not change the recognized scene obtained at time t4 if the recognized scene is on the side deeper than the first specific scene even when the specific scene memory 22 stores the first specific scene. By contrast, if the first specific scene is stored in the specific scene memory 22 and the recognized scene is on the side shallower than the first specific scene, the scene output unit 23 changes the recognized scene in the observation image obtained at time t4 from the esophagus B2 to the stomach B4, which is the actually captured scene. As described above, the scene output unit 23 receives information on the recognized scene from the scene recognition unit 21, refers to the specific scene memory 22, and compares the recognized scene with the first specific scene to output a final scene.

Figure 6:
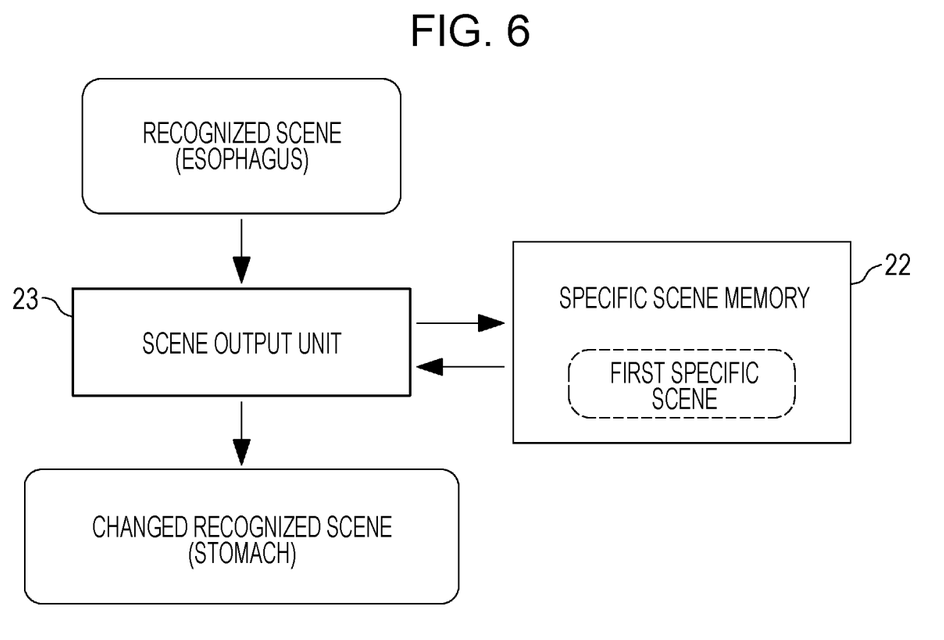
FIG. 6 is an explanatory diagram in which the scene output unit changes a recognized scene in a case where a first specific scene is stored in a specific scene memory.

More specifically, as illustrated in FIG. 6, at time t4 in FIG. 5, if the first specific scene is stored in the specific scene memory 22 and the recognized scene received from the scene recognition unit 21 is the esophagus B2, the scene output unit 23 changes the recognized scene from the esophagus B2 to the stomach B4 because the esophagus B2 is on the side shallower than the esophagogastric junction B3 as the first specific scene.

Figure 7:
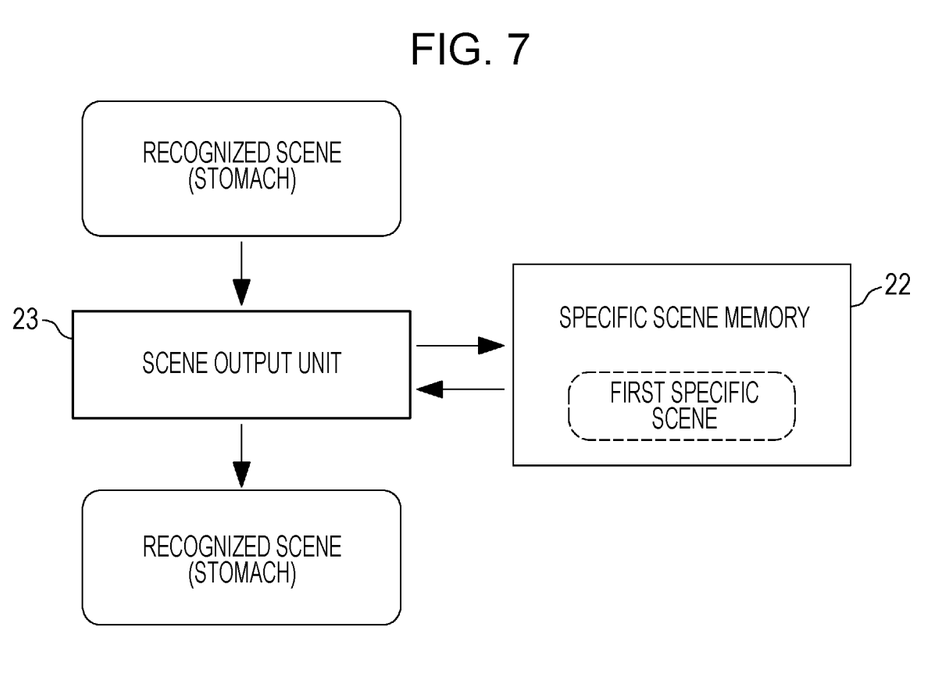
FIG. 7 is an explanatory diagram in which the scene output unit does not change a recognized scene in a case where the first specific scene is stored in the specific scene memory.

As illustrated in FIG. 7, by contrast, at time t3 in FIG. 5, if the first specific scene is stored in the specific scene memory 22 and the recognized scene received from the scene recognition unit 21 is the stomach B4, the scene output unit 23 does not change the recognized scene because the stomach B4 is a scene on the side deeper than the esophagogastric junction B3 as the first specific scene.

Figure 8:
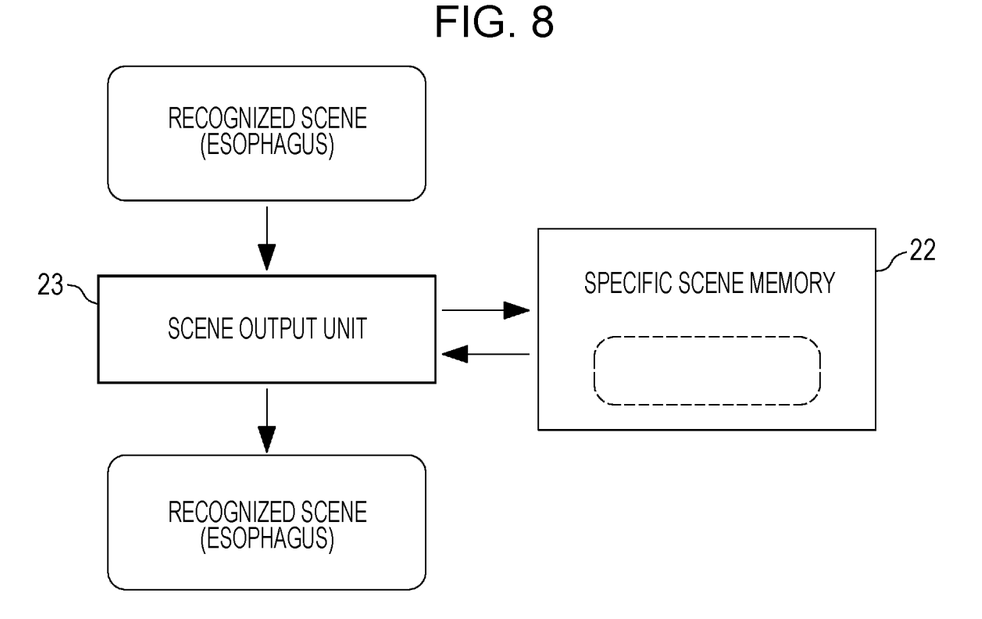
FIG. 8 is an explanatory diagram in which the scene output unit does not change a recognized scene in a case where the first specific scene is not stored in the specific scene memory.

Further, as illustrated in FIG. 8, at time t1 in FIG. 5, the tip part 13a of the endoscope 12 has not passed through the esophagogastric junction B3 as the first specific scene, and no scene is stored in the specific scene memory 22. In this case, the scene output unit 23 outputs the recognized scene without changing the recognized scene.

Figure 9:
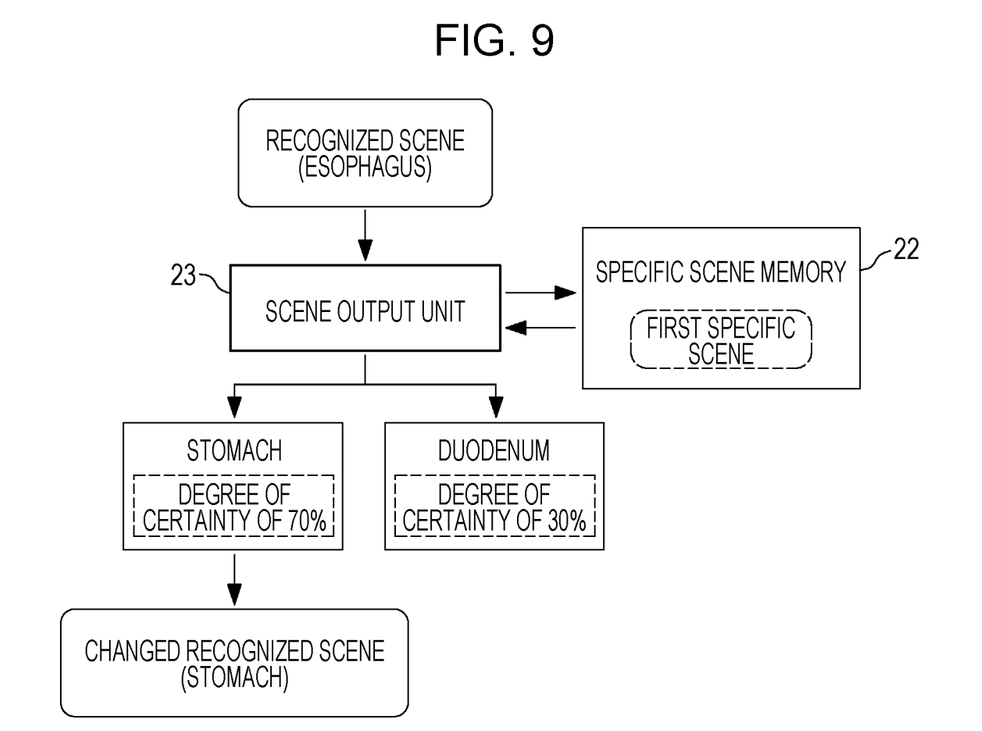
FIG. 9 is an explanatory diagram in a case where the scene output unit changes a recognized scene by using the degree of certainty.

As illustrated in FIG. 9, the scene output unit 23 may change the recognized scene by using the degree of certainty indicating the certainty of the scene. For example, if the esophagogastric junction B3 is stored in the specific scene memory 22 as the first specific scene and the recognized scene is the esophagus B2, the scene output unit 23 changes the recognized scene to a scene having a high degree of certainty among scenes on the side deeper than the esophagogastric junction B3.

Examples of the scenes on the side deeper than the esophagogastric junction B3 include the stomach B4 and the duodenum B5. The scene recognition unit 21 calculates the degree of certainty of the scene on the basis of the observation image. As illustrated in FIG. 9, when the degree of certainty of the stomach B4 is "70%" and the degree of certainty of the duodenum B5 is "30%", it is preferable to change the recognized scene to the stomach B4 having a higher degree of certainty. The degree of certainty can be a numerical value indicating the color tone of each site. For example, the color tones of the surfaces of the stomach and the duodenum are compared with each other. The surface of the stomach is strongly reddish, and the duodenum is strongly yellowish. Each site has such a feature, and, based on such color information, the degree of certainty can be calculated. As another method, the degree of certainty may be calculated on the basis of a correspondence relationship in which the length of insertion of the endoscope 12 is associated with information related to the physique such as the height of the subject.

Figure 10:
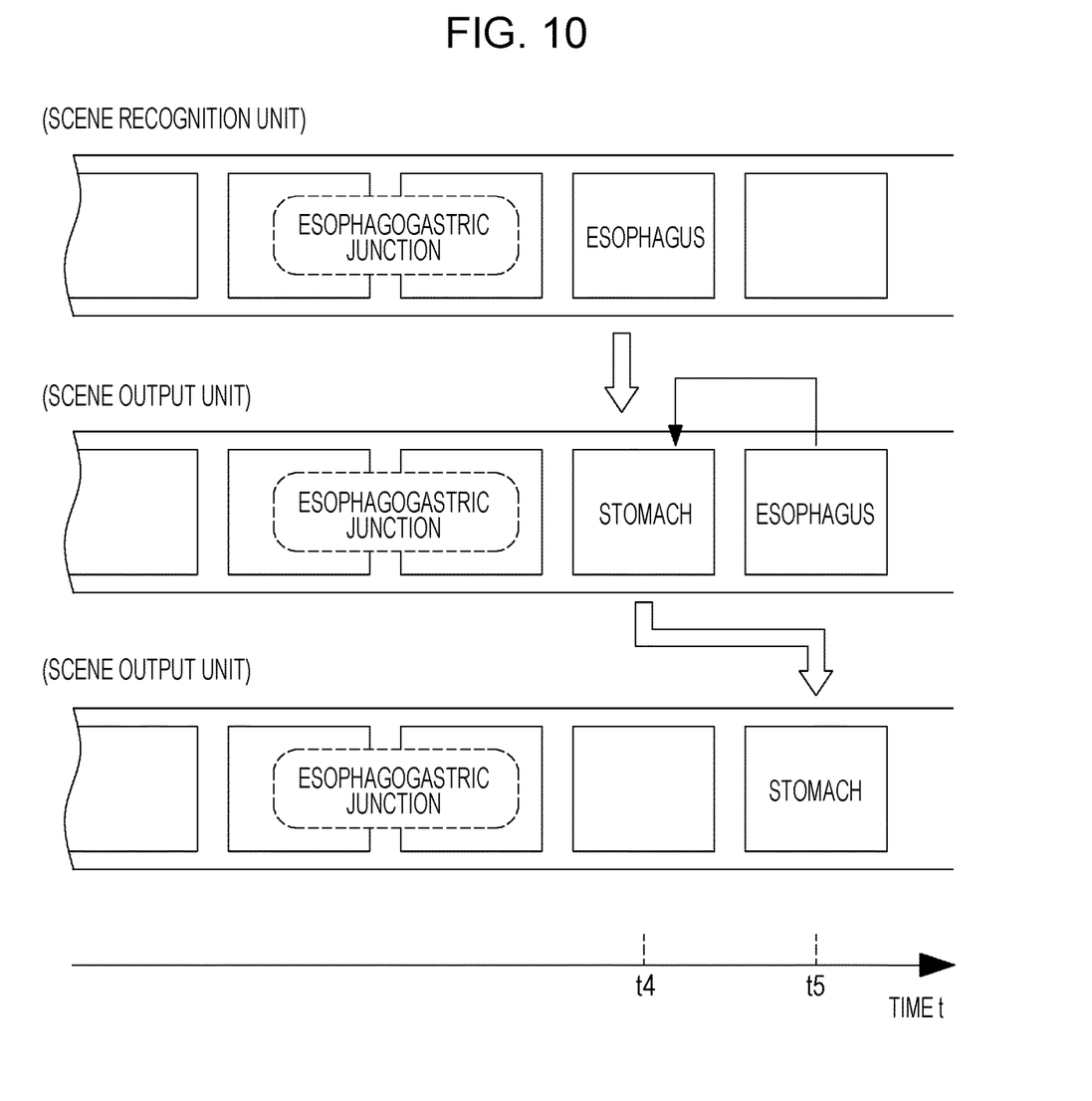
FIG. 10 is an explanatory diagram in a case where the scene output unit changes a recognized scene by using a changed recognized scene.

As illustrated in FIG. 10, the scene output unit 23 can change a recognized scene by using information on a recognized scene changed by the scene output unit 23. For example, if the recognized scene obtained at time t4 is changed from the esophagus B2 to the stomach B4, the scene output unit 23 may compare the recognized scene (the esophagus B2) obtained at time t5 after time t4 with the recognized scene (the stomach B4) obtained at time t4, and change the recognized scene obtained at time t5 to the recognized scene obtained at time t4 if they are different.

Figure 11:
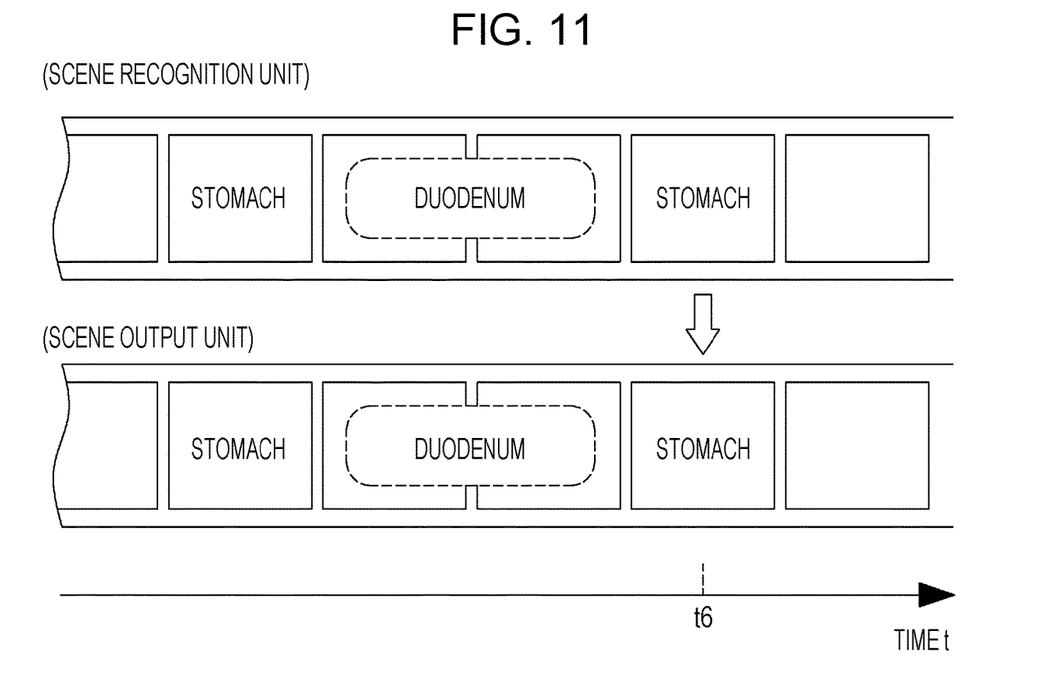
FIG. 11 is an explanatory diagram illustrating observation images of a stomach, a duodenum, and the stomach in chronological order.
Figure 12:
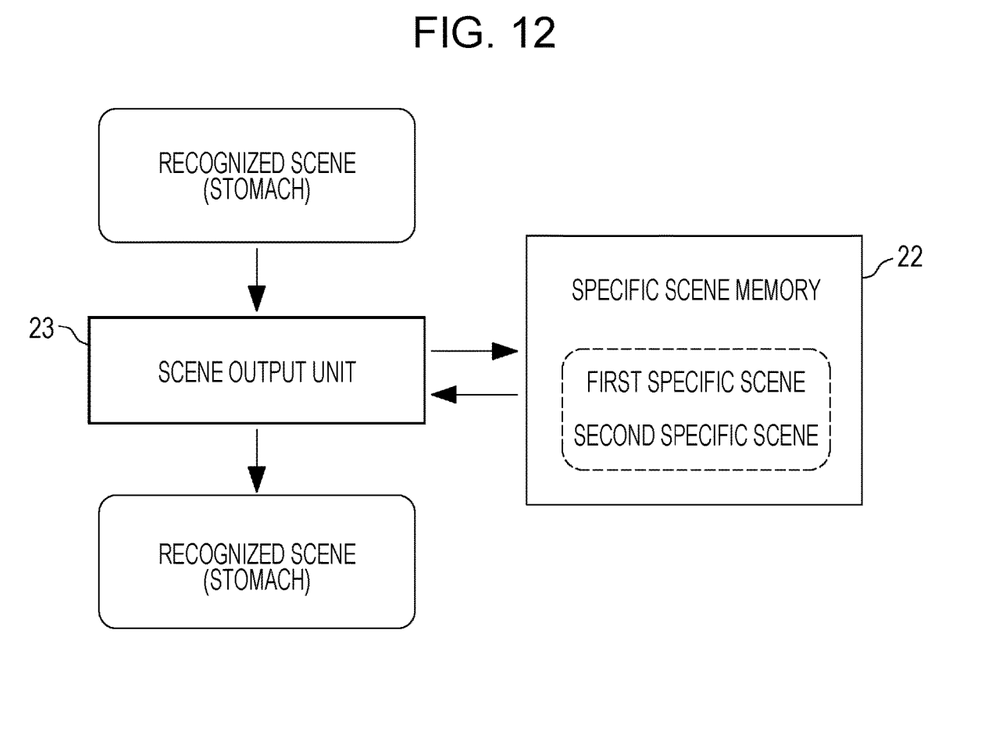
FIG. 12 is an explanatory diagram illustrating functions of the scene output unit in a case where the first specific scene and a second specific scene are stored in the specific scene memory.

As illustrated in FIG. 11, if the tip part 13a of the endoscope 12 reaches the duodenum B5, which is the destination of the forward path F, the duodenum B5 is stored in the specific scene memory 22 as a second specific scene corresponding to the destination of the forward path. As illustrated in FIG. 12, if the first specific scene and the second specific scene are stored in the specific scene memory 22, the scene output unit 23 does not change the recognized scene. For example, the stomach B4, which is a recognized scene obtained at time t6, is not changed.

Figure 13:
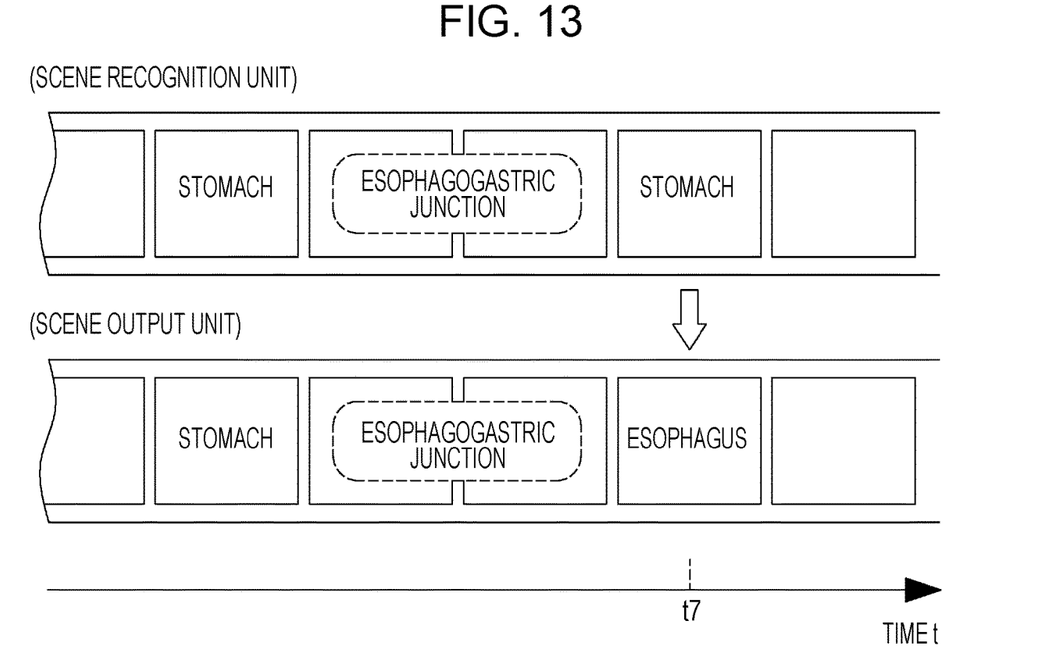
FIG. 13 is an explanatory diagram illustrating functions of the scene recognition unit and the scene output unit in a return path.
Figure 14:
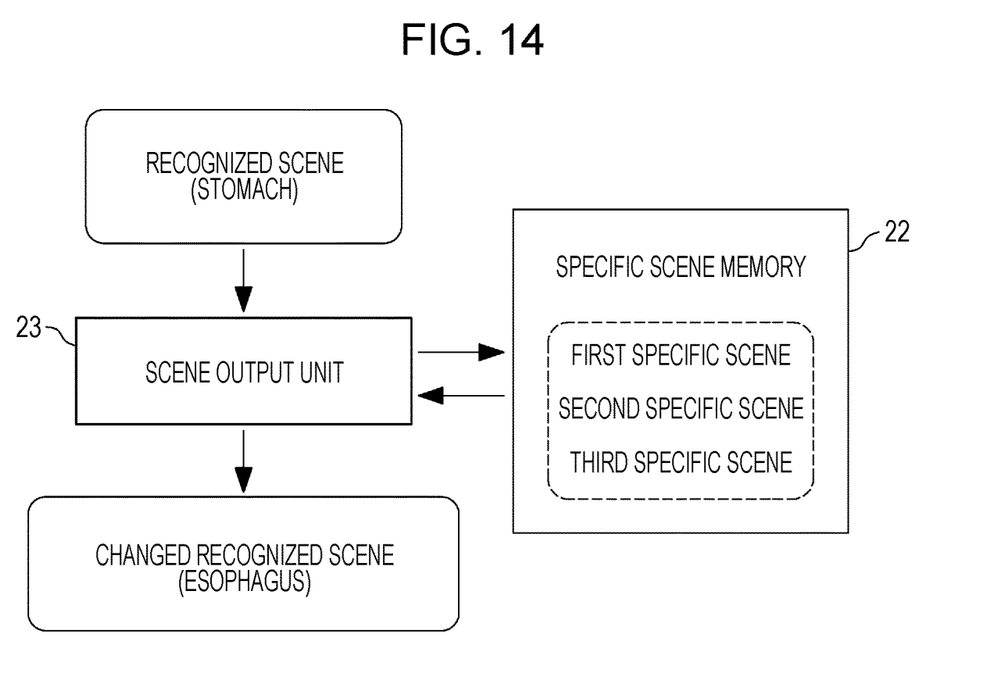
FIG. 14 is an explanatory diagram in which the scene output unit changes a recognized scene in a case where a first, second, and third specific scenes are stored in a specific scene memory.

When the tip part 13a of the endoscope 12 reaches the esophagogastric junction B3 in the return path R, the esophagogastric junction B3 is stored as a third specific scene in the return path R. As illustrated in FIGS. 13 and 14, if the first specific scene, the second specific scene, and the third specific scene are stored in the specific scene memory 22 and a recognized scene obtained at time t7 is the stomach B4 on the side deeper than the third specific scene, the scene output unit 23 changes the recognized scene to either the esophagus B2 or the pharynx B1 on the side shallower than the third specific scene. By contrast, even in a case where the first specific scene, the second specific scene, and the third specific scene are stored in the specific scene memory 22, the scene output unit 23 does not change the recognized scene obtained at time t7 if the recognized scene is on the side shallower than the third specific scene. Even the change of a recognized scene in a case where the first specific scene, the second specific scene, and the third specific scene are stored in the specific scene memory 22 is performed using the method described above such that the recognized scene can be changed to a scene having a high probability by using the degree of certainty or a recognized scene changed by the scene output unit 23 can be used to change a recognized scene that is recognized thereafter.

Figure 15:
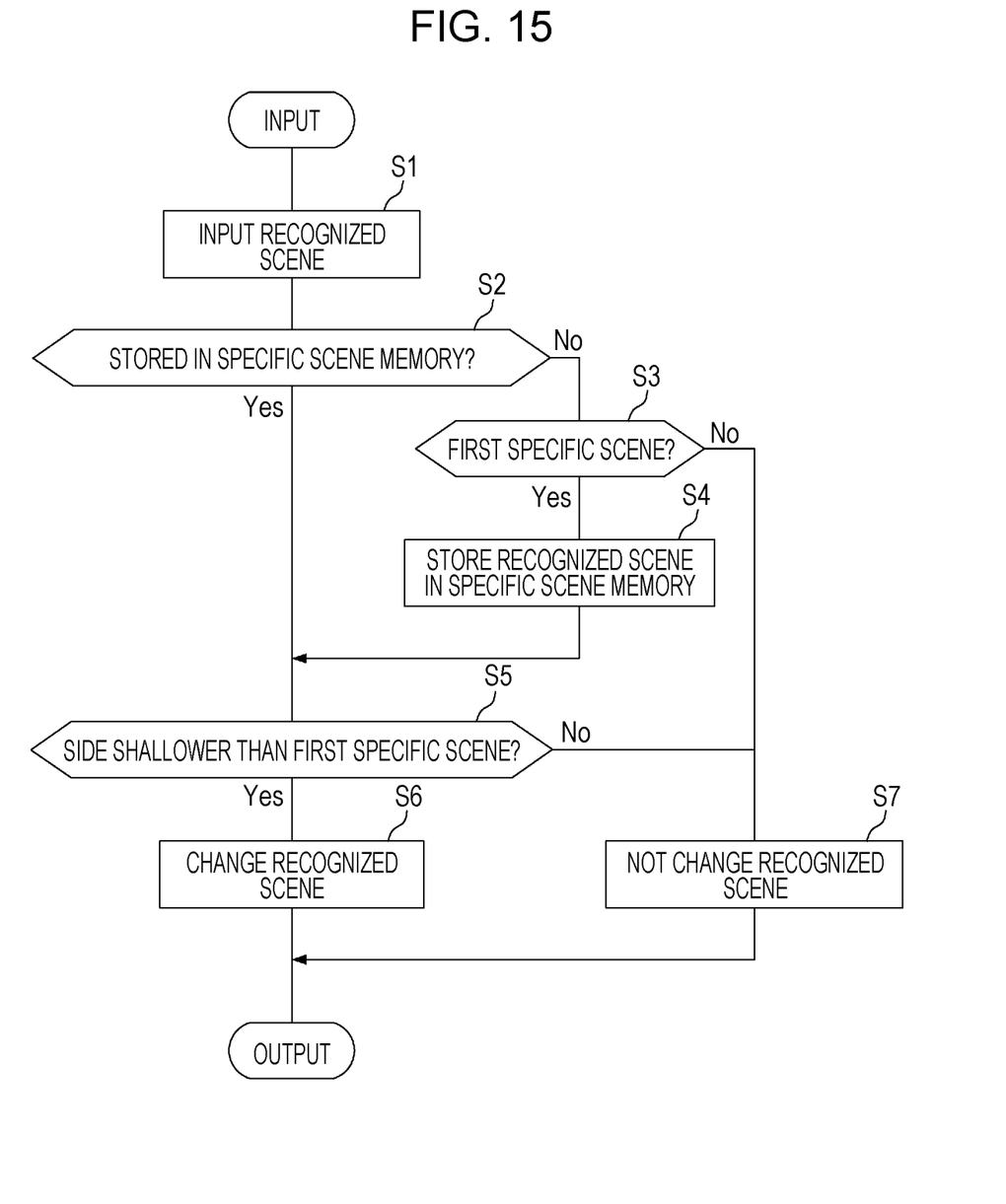
FIG. 15 is a flowchart illustrating functions of the scene output unit in the forward path.

FIG. 15 is a flowchart illustrating the process flow of the scene output unit 23 in the forward path F. Since similar processing is performed in the return path R, only the processing in the forward path F will be described here. First, a recognized scene is input from the scene recognition unit 21 to the scene output unit 23 (step S1). The scene output unit 23 determines whether the first specific scene has been stored in information stored in the specific scene memory 22 (step S2). If no specific scene has been stored, the recognized scene is stored in the specific scene memory 22 when the recognized scene is the first specific scene (steps S3 and S4), and the recognized scene is output without being changed when the recognized scene is not the first specific scene (step S7). If the first specific scene has been stored, or after the first specific scene is stored in the specific scene memory 22, the recognized scene and the first specific scene are compared in order (step S5). If the recognized scene is a scene on the side shallower than the first specific scene, the recognized scene is changed and output (step S6). If the recognized scene is a scene on the side deeper than the first specific scene, the recognized scene is output without being changed (step S7).

Figure 16:
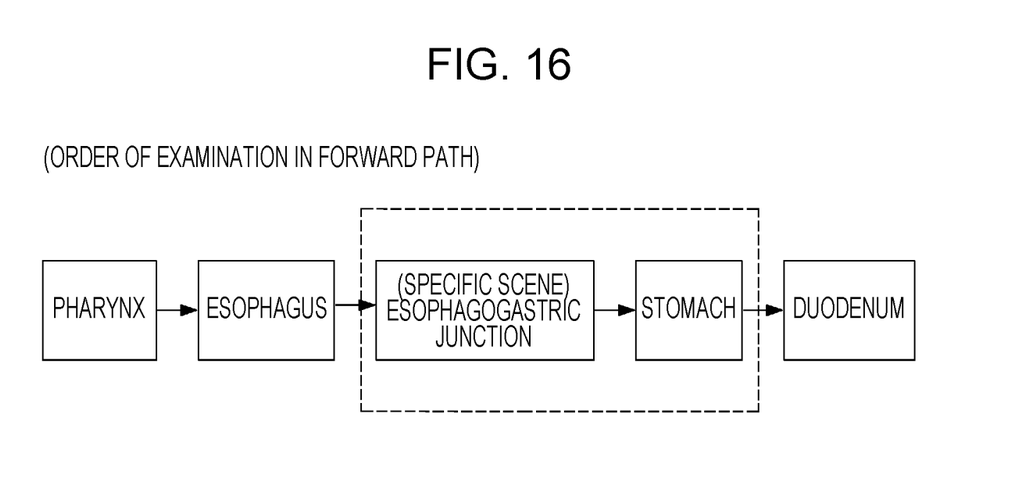
FIG. 16 is an explanatory diagram illustrating the order of examination of the upper digestive tract in the forward path.
Figure 17:
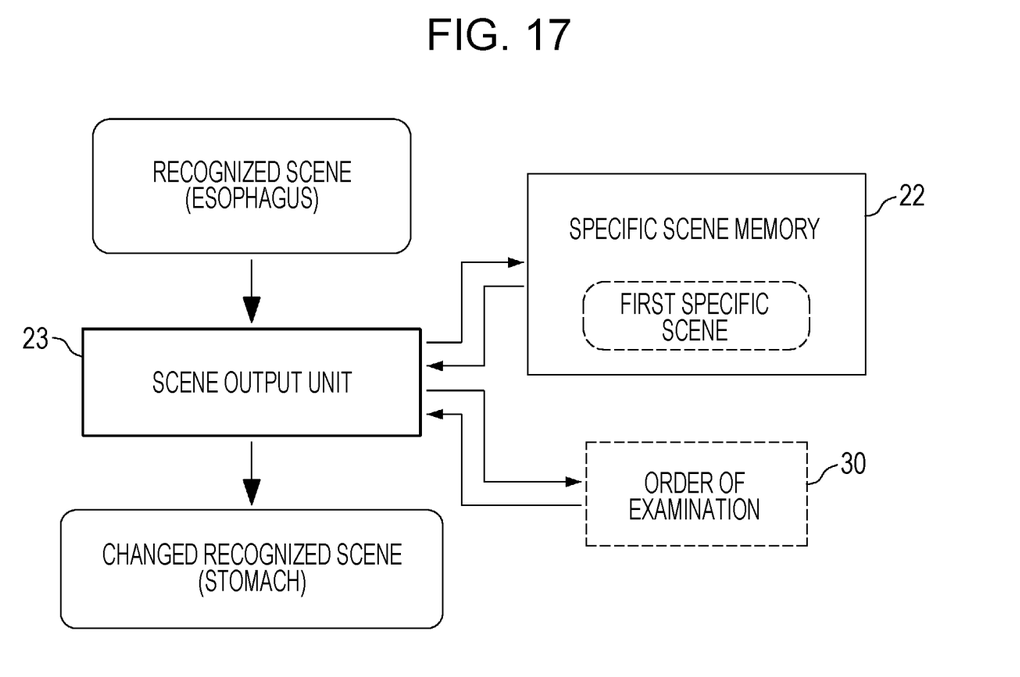
FIG. 17 is an explanatory diagram in a case where the scene output unit changes a recognized scene on the basis of the order of examination.

The screening of the upper digestive tract is performed in a certain direction, for example, from the pharynx B1, which is on the side closer to the subject's mouth, toward the duodenum B5, which is on the side farther away from the subject's mouth, in the forward path F. Accordingly, the order of scenes to be observed may be stored as an order of examination 30, and recognized scenes may be changed such that the order of the specific scenes and the recognized scenes follows the order of examination 30. As illustrated in FIG. 16, in the order of examination 30 in the forward path F, the scene subsequent to the esophagogastric junction B3, which is the first specific scene, is the stomach B4. As illustrated in FIG. 17, in a case where the esophagogastric junction B3 is stored as the first specific scene and the recognized scene is on the side shallower than the first specific scene, the recognized scene is changed from the esophagus B2 to the stomach B4 on the basis of the order of examination 30. The order of examination 30 may be stored in the lesion recognition processing unit 24 in the endoscopic image processing apparatus 16 or in a memory disposed in the endoscopic image processing apparatus 16, or may be stored in an external endoscope information management system or the like.

In a case where the recognized scene obtained after the scene recognition unit 21 recognizes the esophagogastric junction B3 as the first specific scene is not a scene associated with the first specific scene, the recognized scene is preferably changed to a scene on the side deeper than the first specific scene. For example, the scenes associated with the esophagogastric junction B3 are the stomach B4 and the duodenum B5. In this case, the recognized scene obtained after the esophagogastric junction B3 is recognized as the first specific scene is preferably changed to the stomach B4 or the duodenum B5 (see FIG. 3 and the like). Further, for example, in response to the scene recognition unit 21 recognizing a scene other than the upper digestive tract, such as the sigmoid colon, as a recognized scene during the screening examination of the upper digestive tract, the scene output unit 23 preferably changes the recognized scene to the stomach B4 or the duodenum B5 included in the upper digestive tract.

Further, for example, the scene associated with the esophagogastric junction B3 is the stomach B4. In this case, if the recognized scene obtained after the esophagogastric junction B3 is recognized as the first specific scene is different from the stomach B4, the recognized scene may be changed to the stomach B4 until the tip part 13a reaches the duodenum B5 (see FIG. 3 and the like). Likewise, also in the examination in the return path R, in a case where the scene associated with the duodenum B5 is the stomach B4, if the recognized scene obtained after the duodenum B5 is recognized as the second specific scene is different from the stomach B4, the recognized scene may be changed to the stomach B4 until the tip part 13a reaches the esophagogastric junction B3.

In this embodiment, the first specific scene in the forward path F and the third specific scene in the return path R are the same, namely, the esophagogastric junction B3. Alternatively, the first specific scene and the third specific scene may be different from each other such that the first specific scene is the esophagogastric junction B3 and the third specific scene is the esophagus B2.

In this embodiment, the hardware structures of processing units that perform various processes, such as the observation image acquisition unit 20, the scene recognition unit 21, the scene output unit 23, and the lesion recognition processing unit 24, are various processors described below. The various processors include a central processing unit (CPU), which is a general-purpose processor executing software (program) to function as various processing units, a graphical processing unit (GPU), a programmable logic device (PLD) such as a field programmable gate array (FPGA), which is a processor whose circuit configuration is changeable after manufacture, a dedicated electric circuit, which is a processor having a circuit configuration specifically designed to execute various types of processing, and so on.

A single processing unit may be configured as one of the various processors or as a combination of two or more processors of the same type or different types (such as a plurality of FPGAs, a combination of a CPU and an FPGA, or a combination of a CPU and a GPU, for example). Alternatively, a plurality of processing units may be configured as a single processor. Examples of configuring a plurality of processing units as a single processor include, first, a form in which, as typified by a computer such as a client or a server, the single processor is configured as a combination of one or more CPUs and software and the processor functions as the plurality of processing units. The examples include, second, a form in which, as typified by a system on chip (SoC) or the like, a processor is used in which the functions of the entire system including the plurality of processing units are implemented as one IC (Integrated Circuit) chip. As described above, the various processing units are configured by using one or more of the various processors described above as a hardware structure.

More specifically, the hardware structure of these various processors is an electric circuit (circuitry) in which circuit elements such as semiconductor elements are combined. The hardware structure of the storage unit is a storage device such as a hard disc drive (HDD) or a solid state drive (SSD).

REFERENCE SIGNS LIST 10 endoscope system
12 endoscope
13 insertion unit
13A tip part
14 operation portion
15 light source device
16 endoscopic image processing apparatus
18 monitor
19 console
20 observation image acquisition unit
21 scene recognition unit
22 specific scene memory
23 scene output unit
24 lesion recognition processing unit
30 order of examination

What is claimed is:

1. An endoscopic image processing apparatus comprising:
a processor configured to:
acquire an endoscopic observation image captured by an endoscope having an insertion portion to be inserted into a body cavity of a subject, the endoscopic observation image being an observation image of an inside of the body cavity;
recognize a scene by using the endoscopic observation image;
in a case where a recognized scene recognized by the processor is a first specific scene recognized at a time of insertion of the insertion portion, store the recognized scene in a specific scene memory as the first specific scene;
output the recognized scene without changing the recognized scene in a case where the first specific scene is stored in the specific scene memory and the recognized scene is a scene on a side deeper than the first specific scene in a direction of movement of the insertion portion; and
change the recognized scene and output the changed recognized scene in a case where the first specific scene is stored in the specific scene memory and the recognized scene is a scene on a side shallower than the first specific scene in the direction of movement of the insertion portion.

2. The endoscopic image processing apparatus according to claim 1, wherein the processor is configured to, when changing the recognized scene, change the recognized scene to a scene on the side deeper than the first specific scene.

3. The endoscopic image processing apparatus according to claim 2, wherein the processor is configured to change the recognized scene to a scene having a high degree of certainty among scenes on the side deeper than the first specific scene.

4. The endoscopic image processing apparatus according to claim 1, wherein the processor is configured to change the recognized scene to a scene on the side deeper than the first specific scene in a case where the first specific scene is stored in the specific scene memory and the recognized scene is not a scene associated with the first specific scene.

5. The endoscopic image processing apparatus according to claim 1, wherein the processor is configured to change the recognized scene to a scene associated with the first specific scene in a case where the first specific scene is stored in the specific scene memory and the recognized scene is not a scene associated with the first specific scene.

6. The endoscopic image processing apparatus according to claim 1, wherein the processor is configured to, in a case where the recognized scene is a second specific scene at a position where the insertion portion is pulled back in the direction of movement of the insertion portion, store the recognized scene in the specific scene memory as the second specific scene.

7. The endoscopic image processing apparatus according to claim 6, wherein the processor is configured to output the recognized scene without changing the recognized scene in a case where the second specific scene is stored in the specific scene memory.

8. The endoscopic image processing apparatus according to claim 6, wherein the second specific scene is a duodenum.

9. The endoscopic image processing apparatus according to claim 1, wherein the processor is configured to, in a case where the recognized scene is a third specific scene recognized at a time of removal of the insertion portion, store the recognized scene in the specific scene memory as the third specific scene.

10. The endoscopic image processing apparatus according to claim 9, wherein the processor is configured to change the recognized scene and output the changed recognized scene in a case where the recognized scene is a scene on the side deeper than the third specific scene.

11. The endoscopic image processing apparatus according to claim 9, wherein the third specific scene is any one of an esophagus, an esophagogastric junction, or a stomach at the time of removal of the insertion portion.

12. The endoscopic image processing apparatus according to claim 1, wherein the processor is configured to, when changing the recognized scene, change the recognized scene by using a recognized scene changed by the processor.

13. The endoscopic image processing apparatus according to claim 1, wherein the scene includes at least one of a pharynx, an esophagus, an esophagogastric junction, a stomach, or a duodenum.

14. The endoscopic image processing apparatus according to claim 1, wherein the first specific scene is any one of an esophagus, an esophagogastric junction, or a stomach at the time of insertion of the insertion portion.

15. The endoscopic image processing apparatus according to claim 1, wherein the processor is configured to perform lesion recognition processing, the lesion recognition processing being recognition processing for detecting a lesion included in the endoscopic observation image by using the recognized scene that is output.

* * * * *